United States Patent
Marcu

(12) 
(10) Patent No.: US 6,365,722 B1
(45) Date of Patent: Apr. 2, 2002

(54) Y2H14 AN IKK BINDING PROTEIN

(75) Inventor: Kenneth B. Marcu, Stony Brook, NY (US)

(73) Assignee: The Research of State University of New York, Albany, NY (US)

( * ) Notice: Subject to any disclaimer, the term of this patent is extended or adjusted under 35 U.S.C. 154(b) by 0 days.

(21) Appl. No.: 09/195,188

(22) Filed: Nov. 17, 1998

(51) Int. Cl.$^7$ .......................... C07H 21/02; C07K 1/00
(52) U.S. Cl. ...................... 536/23.1; 530/350
(58) Field of Search .......................... 536/23.1; 530/350

(56) References Cited

U.S. PATENT DOCUMENTS

| | | | |
|---|---|---|---|
| 5,162,222 A | 11/1992 | Guarino et al. | 435/240.2 |
| 5,776,717 A | 7/1998 | Cao | 435/15 |
| 5,804,374 A | 9/1998 | Baltimore et al. | 435/6 |

OTHER PUBLICATIONS

Mock et al., "CHUK, a Conserved Helix–Loop–Helix Ubiquitous Kinase, Maps to Human Chromosome 10 and Mouse Chromosome 19", *Genomics* 27:348–351 (1995).

Margery A. Connelly and Kenneth B. Marcu, "CHUK, a New Member of the Helix–Loop–Helix and Leucine Zipper Families of Interacting Proteins, Contains a Serine–Theronine Kinase Catalytic Domain", *Cellular and Molecular Biology Research* 41:537–549 (1995).

Sherrington, et al., "Cloning of a gene bearing missense mutations in early–onset familial Alzheimer's disease", *Nature* 375:754–760 (1995).

DiDonato et al., "A Cytokine–Responsive IκB Kinase That Activates The Transcription Factor NF–κB", *Nature* 38817:548–554 (1997).

Regnier et al., "Identification and Characterization of an IκB Kinase", *Cell* 90:373–383 (1997).

Ilana Stancovski and David Baltimore, "NF–κB Activation: The IκB Kinase Revealed?", *Cell* 91:299–302 (1997).

Woronicz et al., "IκB Kinase–β: NF–κB Activation and Complex Formation with IκB Kinase–α and NIK", *Science* 278:866–869 (1997).

Zandi et al., "The IκB Kinase Complex (IKK) Contains Two Kinase Subunits, IKKα and IKKβ, Necessary for IκB Phosphorylation and NF–κB Activation", *Cell* 91: 243–252 (1997).

*Primary Examiner*—Hankyel Park
(74) *Attorney, Agent, or Firm*—Hoffman & Baron, LLP

(57) ABSTRACT

The present invention provides an isolated IκB kinase binding protein designated Y2H14 and functional equivalents therof. The amino acid sequence of Y2H14, the nucleotide sequence encoding Y2H14, and other related protein and nucleic acid molecules are also provided.

6 Claims, No Drawings

SEQUENCE LISTING

<160> NUMBER OF SEQ ID NOS: 2

<210> SEQ ID NO 1
<211> LENGTH: 394
<212> TYPE: PRT
<213> ORGANISM: Homo sapiens

<400> SEQUENCE: 1

```
Cys Gly Leu Pro Leu Lys Glu Gly Ala Leu Arg Pro Ser Tyr Asp Arg
 1               5                  10                  15

Lys Ser Asp Arg Pro Val Tyr Glu Gly Pro Ser Met Phe Gly Gly Glu
            20                  25                  30

Arg Arg Thr Tyr Pro Glu Glu Arg Met Pro Leu Pro Ala Pro Ser Leu
        35                  40                  45

Ser His Gln Pro Pro Ala Pro Arg Val Glu Lys Lys Pro Glu Ser
    50                  55                  60

Lys Asn Val Asp Asp Ile Leu Lys Pro Pro Gly Arg Glu Ser Arg Pro
65                  70                  75                  80

Glu Arg Ile Val Val Ile Met Arg Gly Leu Pro Gly Ser Gly Lys Thr
                85                  90                  95

His Val Ala Lys Leu Ile Arg Asp Lys Glu Val Glu Phe Gly Gly Pro
            100                 105                 110

Ala Pro Arg Val Leu Ser Leu Asp Asp Tyr Phe Ile Thr Glu Val Glu
        115                 120                 125
```

```
Lys Glu Glu Lys Asp Pro Asp Ser Gly Lys Lys Val Lys Lys Lys Val
        130                 135                 140

Arg Glu Tyr Glu Tyr Glu Ala Glu Met Glu Glu Thr Tyr Arg Thr Ser
145                 150                 155                 160

Met Phe Lys Thr Phe Lys Lys Thr Leu Asp Asp Gly Phe Phe Pro Phe
                165                 170                 175

Ile Ile Leu Asp Ala Ile Asn Asp Arg Val Arg His Phe Asp Gln Phe
                180                 185                 190

Trp Ser Ala Ala Lys Thr Lys Gly Phe Glu Val Tyr Leu Ala Glu Met
        195                 200                 205

Ser Ala Asp Asn Gln Thr Cys Gly Lys Arg Asn Ile His Gly Arg Lys
    210                 215                 220

Leu Lys Glu Ile Asn Lys Met Ala Asp His Trp Glu Thr Ala Pro Arg
225                 230                 235                 240

His Met Met Arg Leu Asp Ile Arg Ser Leu Leu Gln Asp Ala Ala Ile
                245                 250                 255

Glu Glu Val Glu Met Glu Asp Phe Asp Ala Asn Ile Glu Glu Gln Lys
                260                 265                 270

Glu Glu Lys Lys Asp Ala Glu Glu Glu Ser Glu Leu Gly Tyr Ile
        275                 280                 285

Pro Lys Ser Lys Trp Glu Met Asp Thr Ser Glu Ala Lys Leu Asp Lys
        290                 295                 300

Leu Asp Gly Leu Arg Thr Gly Thr Lys Arg Lys Arg Asp Trp Glu Ala
305                 310                 315                 320

Ile Ala Ser Arg Met Glu Asp Tyr Leu Gln Leu Pro Asp Asp Tyr Asp
                325                 330                 335

Thr Arg Ala Ser Glu Pro Gly Lys Lys Arg Val Arg Trp Ala Asp Leu
                340                 345                 350

Glu Glu Lys Lys Asp Ala Asp Arg Lys Arg Ala Ile Gly Phe Val Val
        355                 360                 365

Gly Gln Thr Asp Trp Glu Lys Ile Thr Asp Glu Ser Gly His Leu Ala
    370                 375                 380

Glu Lys Ala Leu Asn Arg Thr Lys Tyr Ile
385                 390

<210> SEQ ID NO 2
<211> LENGTH: 1183
<212> TYPE: DNA
<213> ORGANISM: Homo sapiens

<400> SEQUENCE: 2
ttgtggcttg cccctaaagg agggggcctt aaggccatcc tatgaccgga agtctgaccg      60
accagtctat gaaggaccat ccatgtttgg aggagaacga aggacttatc ctgaggagcg     120
aatgcctctg ccagctcctt cactgagcca ccagccacct ccagctccac gagtcgagaa     180
gaagcctgaa tcaaagaatg tggacgatat tttgaaacca ccgggccggg agagcagacc     240
tgagagaatt gttgttataa tgagaggatt acctggcagt ggaaagacac atgttgcaaa     300
acttattcga gataaggagg tagaatttgg aggacctgca cccagagttc taagcctgga     360
tgattacttc atcactgaag tggaaaaaga agaaaaagat ccagattctg gaagaaagt      420 gaaaagaag gtaagggaat atgaatatga agctgagatg gaggagactt accgcaccag     480
catgttcaaa actttcaaaa agactctgga tgatggcttt tttcccttca tcatcctgga     540
tgccatcaat gacagagtta ggcattttga ccagttttgg agtgcagcaa aaaccaaggg     600
```

-continued

| | | | | |
|---|---|---|---|---|
| atttgaggta | tatttggctg | aaatgagtgc | agataaccag | acttgtggca agagaaatat | 660 |
| tcatggaaga | aagcttaaag | aaataaataa | gatggctgat | cactgggaaa ctgcacctcg | 720 |
| tcacatgatg | cgtctagata | ttcgttcttt | gctgcaagat | gctgctattg aagaggtaga | 780 |
| gatggaagat | tttgatgcaa | atatcgaaga | acagaaagaa | gaaagaaag atgcagagga | 840 |
| agaggaaagc | gaactgggtt | acattccgaa | aagcaaatgg | gagatggaca catctgaggc | 900 |
| aaagctagac | aagttggatg | gcttgaggac | tggtactaaa | aggaaacgtg actgggaggc | 960 |
| cattgccagc | agaatggagg | attatcttca | gctccccgat | gattatgata ctcgtgcttc | 1020 |
| tgagcctggg | aagaagaggg | tcagatgggc | agacctggaa | gagaagaagg atgcagatag | 1080 |
| gaaaagggcc | ataggttttg | tggtcggaca | gactgattgg | gagaagatca cagatgaaag | 1140 |
| tggtcacctg | gctgaaaaag | ccctcaatcg | aaccaaatat | ata | 1183 |

Y2H14 AN IKK BINDING PROTEIN

BACKGROUND OF THE INVENTION

The NF-κB family of transcription factors are involved in the regulation of a wide variety of cellular responses. These transcription factors mediate extracellular signals that induce expression of genes involved in such diverse processes as cell division, inflammation, and apoptosis. See, for example, Baldwin, Annu. Rev. Immunol. 12, 141–179 (1996); Beg and Baltimore, Science 274, 782–274 (1996); Gilmore et al., Oncogene 13, 1267–1378 (1996); Mayo, et al, Science 278, 1812–1815 (1997); and Van Antwerp et al., Science 274, 787–789 (1996); Ashkenazi and Dixit, Science 281, 1305–1308 (1998).

NF-κB is anchored in the cytoplasm of most non-stimulated cells by a non-covalent interaction with one of several inhibitory proteins known as IκBS. See for example, Baeuerle and Baltimore, Science 242, 540–546 (1988). Cellular stimuli associated with immune and inflammatory responses, for example inflammatory cytokines such as tumor necrosis factor α (TNFα) or interleukin-1 (IL-1), activate kinases, which in turn activate NF-κB by phosphorylating IκBs. The kinases that phosphorylate IκBs are called IκB kinases (IKKs).

Phosphorylation marks the IκBs for ubiquitination and proteosome mediated degradation. The degradation and dissociation of IκBs from NF-κB unmasks the NF-κB nuclear localization signal, and facilitates the nuclear translocation of active NF-κB to the nucleus, thereby upregulating NF-κB responsive target genes. See, for example, Baeuerle and Henkel, Annu. Rev. Immunol. 12, 141–179 (1994); Baldwin, Annu.Rev. Immunol. 14, 649–683 (1996); Siebenlist et al., Annu.Rev.Cell Biol. 12, 405–455 (1994); and Verma et al, Genes Dev. 9, 2723–2735 (1995). Thus, this phosphorylation of IκBs is a key regulatory step for NF-κB mediated processes.

The determination and characterization of kinases that directly phosphorylate IκBs are instrumental in the delineation of signaling pathways involving NF-κB activation. Recently, an IκB kinase, designated IKKα but also referred to as CHUK (conserved helix-loop-helix ubiquitous kinase), was identified in a yeast-two-hybrid screen with NIK as bait. Regnier et al., Cell 90, 373–383 (1997). IKKα was determined to be responsible for the major IκB kinase activity induced by TNF stimulation of HeLa cells. DiDonato et al., Nature 388, 548–554 (1997). The identification of IKKα as a cytoplasmic kinase which phosphorylates IκB family members at their physiologically relevant sites and targets them for proteosome-mediated degradation was a major breakthrough.

The IKKα gene encodes a 745 amino-acid polypeptide (having a molecular mass of approximately 85 kDa). Murine and human IKKα cDNA clones were found to be almost identical. Connelly and Marcu, Cellular and Molecular Biology Research 41, 537–549 (1995).

Another kinase, termed IKKβ, homologous to IKKα, has also been reported. Stancovski and Baltimore, Cell 91, 299–302 (1997); Woronicz et al., Science 278, 866–869 (1997); and Zandi et al., Cell 91, 243–252 (1997). IKKα and IKKβ have 52% overall similarity to each other and 65% identity in the kinase domain. Zandi et al., Cell 91, 243–252 (1997). An IκB kinase termed T2K has also been described in U.S. Pat. No. 5,776,717 to Cao.

The known IκB protein kinases generally phosphorylate IκBs at specific serine residues. For example, they specifically phosphorylate serines 32 and 36 of IκBα. Phosphorylation of both sites is required to efficiently target IκBα for destruction in vivo. Moreover, activation of IKKα and IKKβ occurs in response to NF-κB activating agents and mutant IKKα and IKKβ that are catalytically inactive block NF-κB stimulation by cytokines. These results highlight the important role played by IκB protein kinases in NF-κB activation processes. See Stancovski and Baltimore, Cell 91, 299–302 (1997) for a recent discussion of IκB kinases.

IKKα and IKKβ have structural motifs characteristic of the IKK kinases. This includes an amino terminal serine-threonine kinase domain separated from a carboxyl proximal helix-loop-helix (H-L-H) domain by a leucine zipper domain. These structural characteristics are unlike other kinases, and the domains are thought to be involved in protein-protein interactions.

Numerous proteins are involved in the signaling pathways that lead to immune, inflammatory, and apoptotic responses. A complete elucidation of these processes requires the identification of additional proteins that are involved and a determination of the protein interactions.

The discovery of additional proteins involved in these processes is important for controlling immune, apoptotic, and inflammatory processes. Thus, there is a great need for the identification and characterizion of additional proteins involved in IKK mediated cellular processes.

SUMMARY OF THE INVENTION

The present invention provides an isolated IKK binding protein comprising the amino acid sequence set forth in SEQ ID NO:1 and functional equivalents. Also included are isolated nucleic acid molecules that encode the IKK binding protein comprising the amino acid sequence set forth in SEQ ID NO: 1 and its functional equivalents, methods of making the IKK binding proteins comprising expressing nucleic acid molecules encoding the proteins, and antibodies directed to the IKK binding proteins.

DETAILED DESCRIPTION OF THE INVENTION

The invention is directed to an IKK binding protein, designated Y2H14, and its functional equivalents. Y2H14 will hereinafter refer to the protein defined by SEQ ID NO:1, which is found in humans.

In this specification, functional equivalents are proteins or fragments that are substantially homologous to SEQ ID NO:1 and that specifically bind to an IKK protein, such as IKKα or IKKβ. The term IKK is used herein to refer to all kinases that phosphorylate any IκB and that have helix-loop-helix and leucine zipper domains. Y2H14 and its functional equivalents bind to the region of the IKK proteins made up of the contiguous helix-loop-helix and leucine zipper domains.

In order to determine whether the sequence of a first protein, or fragment thereof, is substantially homologous to the sequence of a second protein, such as Y2H14, or fragment thereof, the sequences are first aligned so as to optimize the percent of amino acid residues that are identical, or that are identical or equivalent, at corresponding positions. Gaps may be introduced in the sequences, if necessary, to achieve optimization.

Amino acids generally considered to be equivalent are indicated below in separate rows (a) through (e):

(a) Ala (A), Ser (S), Thr (T), Pro (P), Gly (G)
(b) Asn (N), Asp (D), Glu (E), Gln (Q)
(c) His (H), Arg (R), Lys (K)

(d) Met (M), Leu (L), Ile (I), Val (V)

(e) Phe (F), Tyr (Y), Trp (W)

The amino acid sequences of highly homologous proteins can usually be aligned by visual inspection. If visual inspection is insufficient, the proteins are aligned in accordance with any of the methods described by George, D. G. et al, in *Macromolecular Sequencing and Synthesis, Selected Methods and Applications*, pages 127–149, Alan R. Liss, Inc. (1988), such as the formula described at page 137 using a match score of 1, a mismatch score of 0, and a gap penalty of −1.

In a first embodiment, the sequence of a protein or fragment thereof is considered substantially homologous to the sequence of Y2H14 or a fragment thereof if the amino acid sequences, after alignment, are at least about 25% identical, preferably at least about 35% identical, more preferably at least about 50% identical, even more preferably at least about 65% identical, still more preferably at least about 75% identical, most preferably at least about 85% identical, and, ideally at least about 95% identical.

In a second embodiment, the sequence of a protein or fragment thereof is considered substantially homologous to the sequence of Y2H14 or a fragment thereof if the amino acid sequences, after alignment, are at least about 50% identical or equivalent, preferably at least about 65% identical or equivalent, most preferably at least about 85% identical or equiavalent, and ideally at least about 95% identical or equivalent.

Functional equivalents include all modifications of the polypeptide set forth in SEQ ID NO:1. These modifications may be introduced deliberately, as by site-directed mutagenesis, or may be natural variations and mutations. Such modifications include substitutions, additions, and/or deletions in the protein sequences as long as substantial homology and specific binding to IKK proteins are maintained.

For example, functional equivalents include variant Y2H14 proteins that are expressed by naturally occurring alleles. Alleles are alternative forms of a gene that occupy a given locus of a chromosome within a species.

Functional equivalents of Y2H14 also include proteins from non-human mammalian species (species orthologs) as well as proteins expressed by alleles of such species orthologs. Non-human mammals include, for example, primates, pet animals such as dogs and cats, laboratory animals such as rats and mice, and farm animals such as horses, sheep, and cows.

The proteins of the invention that do not occur in nature are isolated. The term "isolated" as used herein, in the context of proteins, refers to a polypeptide which is unaccompanied by at least some of the material with which it is associated in its natural state. The isolated protein constitutes at least 0.5%, preferably at least 5%, more preferably at least 25% and still more preferably at least 50% by weight of the total protein in a given sample.

Most preferably the "isolated" protein is substantially free of other proteins, lipids, carbohydrates or other materials with which it is naturally associated, and yields a single major band on a non-reducing polyacrylamide gel. Substantially free means that the protein is at least 75%, preferably at least 85%, more preferably at least 95% and most preferably at least 99% free of other proteins, lipids, carbohydrates or other materials with which it is naturally associated.

The invention also provides novel and/or isolated nucleic acid molecules that encode SEQ ID NO:1 and the functional equivalents thereof Nucleic acid molecules (nucleic acids) of the invention include deoxyribonucleic acid (DNA), complementary DNA (cDNA), and ribonucleic acid (RNA) sequences.

For example, the invention includes an isolated nucleic acid molecule as set forth in SEQ ID NO:2, isolated nucleic acid molecules that are substantially homologous with SEQ ID NO:2, isolated nucleic acid molecules that hybridize with SEQ ID NO:2 under stringent conditions, nucleic acid sequences that are degenerate as a result of the genetic code, and the complements and fragments thereof In order to determine whether the sequence of a first nucleic acid molecule, or fragment thereof, is substantially homologous to the sequence of a second nucleic acid molecule, such as SEQ ID NO: 2, or fragment thereof, the sequences are first aligned so as to optimize the percent of nucleotides that are identical at corresponding positions. Gaps may be introduced in the sequences if necessary to achieve optimization.

The nucleic acid sequences of highly homologous nucleic acid molecules can usually be aligned by visual inspection. If visual inspection is insufficient, the nucleic acid molecules are aligned in accordance with any of the methods described by George, D. G. et al, in *Macromolecular Sequencing and Synthesis, Selected Methods and Applications*, pages 127–149, Alan R. Liss, Inc. (1988), such as the formula described at page 137 using a match score of 1, a mismatch score of 0, and a gap penalty of −1.

In the present specification, the sequence of a nucleic acid molecule or fragment thereof is considered substantially homologous to SEQ ID NO:2, or a fragment thereof, if the nucleic acid sequences, after alignment, are at least about 40% identical, preferably at least about 50% identical, more preferably at least about 60% identical, even more preferably at least about 70% identical, still more preferably at least about 80% identical, most preferably at least about 90% identical, and, ideally at least about 95% identical.

The invention also includes nucleic acid molecules that hybridize to SEQ ID NO:2, a fragment of SEQ ID NO:2, a complement of SEQ ID NO:2, or a complement of a fragment of SEQ ID NO:2 under stringent conditions.

Also included in the invention are a preferred group of protein functional equivalents of SEQ ID NO:1 encoded by nucleic acid molecules that hybridize under stringent conditions to a sequence complementary to SEQ ID NO:2 or a fragment of SEQ ID NO:2.

The term "stringent conditions," as used herein, is equivalent to "high stringent conditions" and "high stringency." These terms are used interchangeably in the art.

Stringent conditions are defined in a number of ways. In one definition, stringent conditions are selected to be about 50° C. lower than the thermal melting point ($T_m$) for a specific sequence at a defined ionic strength and pH. The $T_m$ is the temperature (under defined ionic strength and pH) at which 50% of the target sequence hybridizes to a perfectly matched sequence. Typical stringent conditions are those in which the salt concentration is about 0.02 M at pH 7 and the temperature is at least about 60° C. Further examples of stringent conditions can be found in U.S. Pat. No. 5,789,550 to Goeddel et al. (1998). The description of stringent conditions in U.S. Pat. No. 5,789,550 is herein incorporated by reference.

Stringent conditions, in the nucleic acid hybridization context, include a combination of conditions, such as the nature and concentration of salts and organic solvents, temperature, and other parameters that are typically known to control hybridization reactions. The combination of parameters is more important than the measure of any single parameter. See U.S. Pat No. 5,786,210; Wetmur and Davidson, J. Mol. Biol. 31, 349–370 (1968). Generally, stringent conditions are obtained at higher temperatures and lower ionic strength. Control of hybridization conditions, and the relationships between hybridization conditions and degree of homology are understood by those skilled in the art. See, for example, Bej, A. K., Nucleic Acid Hybridizations: Principles and Strategies, in Dangler, C. A. ed, *Nucleic Acid Analysis: Principles and Bioapplications*, Wiley-Liss, Inc., pp. 1–29 (1996); Adams et al., *The Biochemistry of the Nucleic Acids*, pp. 605–606, Chapman & Hall (1992); Sambrook J, Fritsch EF, and Maniatis T, *Molecular Cloning. A Laboratory Manual*, 2d ed., Cold Spring Harbor Laboratory, Cold Spring Harbor (1989).

Fragments of nucleic acid molecules of the invention include primers and probes which are useful as tools in molecular biology and biotechnology. The fragment may or may not encode a polypeptide that binds to IKKα or IKKβ. Even if the encoded polypeptide does not bind, the fragment can be used, for example, as a primer ("amplimer") to selectively amplify nucleic acid, such as genomic DNA or total RNA. Primers can also be used in nucleic acid amplification procedures such as the polymerase chain reaction (PCR), ligase chain reaction (LCR), repair chain reaction (RCR), PCR oligonucleotide ligation assay (PCR-OLA), and the like.

Fragments of the nucleic acid molecules of the invention can also be oligonucleotides complementary to a target nucleic acid molecule, i.e., the fragment can be a probe. Such oligonucleotides can be DNA or RNA. Oligonucleotides useful as probes in hybridization studies, such as in situ hybridization, can also be constructed.

The length of the oligonucleotide probe is not critical, as long as it is capable of hybridizing to the target molecule. The oligonucleotide should contain at least 6 nucleotides, preferably at least 10 nucleotides, and more preferably, at least 15 nucleotides. There is no upper limit to the length of the oligonucleotide probes. Longer probes are more difficult to prepare and require longer hybridization times. Therefore, the probe should not be longer than necessary. Normally, the oligonucleotide probe will not contain more than 50 nucleotides, preferably not more than 40 nucleotides, and, more preferably, not more than 30 nucleotides.

Numerous methods for detectably labeling such probes with radioisotopes, fluorescent tags, enzymes, binding moieties (e.g., biotin), and the like are known, so that the probes of the invention can be adapted for easy detectability. Methods for making and using nucleic acid probes are understood by those skilled in the art. See, for example, Keller G H and Manak M M, *DNA Probes*, 2d ed., Macmillan Publishers Ltd., England (1991) and Hames B D and Higgins S J, eds., *Gene Probes I and Gene Probes II*, IRL Press, Oxford (1995).

The nucleic acid molecules may contain synthetic sequences that do not occur in nature and/or they are isolated. The term "isolated," as used herein, in the context of nucleic acids, includes nucleic acid molecules unaccompanied by at least some of the material with which they are associated in their natural state. The isolated nucleic acid may constitute at least 0.5%, preferably at least 5%, more preferably at least 25% and still more preferably at least 50% by weight of the total nucleic acid in a given sample. Most preferably the "isolated" nucleic acid is substantially free of other nucleic acids, proteins, lipids, carbohydrates or other materials with which it is naturally associated. Substantially free means that the nucleic acid is at least 75%, preferably at least 85%, more preferably at least 95% and most preferably at least 99% free of other nucleic acids, proteins, lipids, carbohydrates or other materials with which it is naturally associated. The nucleic acid molecules of the invention can also be recombinant, meaning that they comprise a non-natural sequence or a natural sequence joined to nucleotide(s) other those in which they are joined on the natural chromosome.

Y2H14 was shown, using yeast two-hybrid screens, to bind to the carboxyl terminal domain regions of IKKα and IKKβ. See example 1. Y2H14 specifically binds with the region of the IKK proteins made up of the contiguous helix-loop-helix and leucine zipper domains. The binding of the Y2H14 protein to the IKKs is about the same as the binding of IKKα to a natural substrate of IKKα, viz. IκBβ2.

The Y2H14 protein and the other IKK binding proteins described in example 1 are useful for elucidating and controlling pathways leading to inflammation and apoptosis. These processes are mediated by receptors such as tumor necrosis factor (TNF) receptors. The IKK binding proteins can also be used to detect IKK complexes and modulate IKK activity in cells undergoing signalling by inflammatory mediators such as TNFα and Il-1.

The Y2H14 and its functional equivalents are also useful for identifying therapeutically active agents that modulate the binding or interaction of Y2H14 and either IKKα or IKKβ. Such agents can either prevent the formation of Y2H14/IKK complexes or prevent or inhibit the dissociation of Y2H14/IKK complexes. Molecules that prevent the formation of Y2H14/IKK complexes or inhibit the dissociation of these complexes are useful for boosting the immune system, or as immunosuppresants, or as antiinflammatory agents.

Complex formation or dissociation can be determined by methods well known in the art. Such methods include, for example, gel filtration, sucrose density gradient centrifugation, crosslinking, and immunoprecipitation.

The proteins and variants of the proteins can be prepared by methods known in the art. Such methods include isolating the protein directly from cells, and synthesizing the protein chemically from individual amino acids. Preferably, the proteins of the invention can be prepared by providing DNA that encodes the protein, amplifying or cloning the DNA, expressing the DNA in a suitable host, and harvesting the protein.

DNA encoding the proteins of the invention can be synthesized or isolated. The DNA of the invention can be synthesized chemically from the four nucleotides in whole or in part by methods known in the art. Such methods include those described by Caruthers, Science 230, 281–285 (1985). DNA can also be synthesized by preparing overlapping double-stranded oligonucleotides, filling in the gaps, and ligating the ends together. See, generally, Sambrook et al. (1989) and Glover D M and Hames B D, eds., *DNA Cloning*, 2d ed., Vols. 1–4, IRL Press, Oxford (1995).

DNA expressing functional homologs of the protein can be prepared from wild-type DNA by site-directed mutagenesis. See, for example, Zoller and Smith, Nucleic Acids Res 10, 6487–6500 (1982); Zoller, Methods Enzymol 100, 468–500 (1983); Zoller, DNA 3(6), 479–488 (1984); and McPherson, ed., *Directed Mutagenesis: A Practical Approach*, IRL Press, Oxford (1991).

DNA encoding the protein of the invention can be isolated from different species by using the human sequence, SEQ ID NO:2, to prepare one or more oligonucleotide probes. The probe is labeled and used to screen a genomic or cDNA library in a suitable vector, such as phage lambda. The homology between the DNA of the Y2H14 of the species being screened and that of the human DNA is taken into account in determining the conditions of hybridization. The cDNA library may be prepared from mRNA by known methods, such as those described in Gubler and Hoffman, Gene 25, 263–270 (1983). Oligonucleotide probes can be used to screen cDNA libraries from different species and tissues. The oligonucleotide probe should be labeled so that it can be detected upon hybridization to DNA in the library being screened. These methods are well known in the art.

The DNA isolated is sequenced, and the sequence used to prepare additional oligonucleotide probes. This procedure may be repeated to obtain overlapping fragments until a complete open reading frame is produced.

The nucleic acids of the invention may be amplified by methods known in the art. One suitable method is the polymerase chain reaction (PCR) method described by Saiki et al., Science 239, 487 (1988), Mullis et al in U.S. Pat. No. 4,683,195 and by Sambrook et al. (1989). It is convenient to amplify the clones in the lambda-gt10 or lambda-gt11 vectors using lambda-gt10 or lambda-gt11-specific oligomers as the amplimers (available from Clontech, Palo Alto, Calif.). Other amplification procedures that are well known in the art such as ligase chain reaction (LCR), repair chain reaction (RCR), and PCR oligonucleotide ligation assay (PCR-OLA) can also be used to amplify the nucleic acids of the invention.

DNA encoding the proteins of the invention, or unique fragments thereof, may also be cloned in a suitable host cell and expressed by methods well known in the art. The DNA and protein may be recovered from the host cell. See, generally, Sambrook et al. (1989), for methods relating to the manufacture and manipulation of nucleic acids. The entire gene or additional fragments of the gene can be isolated by using the known DNA sequence or a fragment thereof as a probe. To do so, restriction fragments from a genomic or cDNA library may be identified by Southern hybridization using labeled oligonucleotide probes derived from SEQ ID NO:2.

The amplified or cloned DNA can be expressed in a suitable expression vector by methods known in the art. See, generally, Sambrook et al. (1989).

A variety of expression vectors and host cell systems can be used. These include, for example, microorganisms such as bacteria transformed with recombinant bacteriophage DNA, plasmid DNA, or cosmid DNA containing the Y2H14 coding region. Other expression vectors and host cell systems that can be used include yeast transformed with recombinant yeast expression vectors containing the Y2H14 coding sequence, insect cells infected with recombinant virus expression vectors containing the Y2H14 coding sequence, plant cells infected with recombinant virus expression vectors containing the Y2H14 coding sequence, or animal cells infected with recombinant virus expression vectors (e.g., retroviruses, adenovirus, vaccinia virus) containing the Y2H14 coding sequence.

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Useful expression hosts include well-known prokaryotic and eukaryotic cells. Some suitable prokaryotic hosts include, for example, E. coli, such as E. coli SG-936, E. coli HB 101, E. coli W3 110, E. coli X1776, E. coli X2282, E. coli DHI, and E. coli MRCl, Pseudomonas sp., Bacillus sp., such as B. subtilis, and Streptomyces sp. Suitable eukaryotic cells include yeasts and other fungi, insect, animal cells, such as COS cells and CHO cells, human cells and plant cells in tissue culture.

Preferably, Y2H14 and its functional equivalents are expressed using baculoviral vectors in insect cell cultures. In general, the transformation of insect cells and production of foreign proteins therein is disclosed in Guarino et al., U.S. Pat. No. 5,162,222.

Proteins can be isolated from a solubilized fraction by standard methods. Some suitable methods include precipitation and liquid chromatographic protocols such as ion exchange, hydrophobic interaction, and gel filtration. See, for example, *Methods Enzymol* (*Guide to Protein Chemistry*, Deutscher, ed., Section VII) pp. 182:309 (1990) and Scopes, *Protein Purification*, Springer-Verlag, New York (1987), which are herein incorporated by reference.

Alternatively, purified material is obtained by separating the protein on preparative SDS-PAGE gels, slicing out the band of interest and electroeluting the protein from the polyacrylamide matrix by methods known in the art. The detergent SDS is removed from the protein by known methods, such as by dialysis or the use of a suitable column, such as the Extracti-Gel column from Pierce. Mixtures of proteins can be separated by, for example, SDS-PAGE in accordance with the method of Laemmli, Nature 227, 680–685 (1970). Such methods are well known in the art.

The proteins of the invention can also be chemically synthesized by methods known in the art. Suitable methods for synthesizing proteins are described by Stuart and Young, Solid Phase *Peptide Synthesis*, 2d ed., Pierce Chemical Company (1984).

The invention also includes an antibodies or antibody fragments that specifically bind to epitopes of the proteins of the invention defined by the amino acid sequence set forth in SEQ ID NO:1. An "antibody" in accordance with the present specification is defined broadly as a protein that binds specifically to an epitope. The antibodies of the invention can be monoclonal antibodies, polyclonal antibodies, chimerized antibodies, humanized antibodies, single chain antibodies, or a fragment thereof For use in in vivo applications with human subjects, the antibody is preferably chimerized or humanized, containing an antigen binding region from, e.g., a rodent, with the bulk of the antibody replaced with sequences derived from human immunoglobulin.

Antibodies further include recombinant polyclonal or monoclonal Fab fragments prepared in accordance with the method of Huse et al., Science 246, 1275–1281 (1989).

Polyclonal antibodies are isolated from mammals that have been inoculated with the protein or a functional analog in accordance with methods known in the art. Briefly, polyclonal antibodies may be produced by injecting a host mammal, such as a rabbit, mouse, rat, or goat, with the protein or a fragment thereof capable of producing antibodies that distinguish between mutant and wild-type protein.

The peptide or peptide fragment injected may contain the wild-type sequence or the mutant sequence. Sera from the mammal are extracted and screened to obtain polyclonal antibodies that are specific to the peptide or peptide fragment.

The antibodies are preferably monoclonal. Monoclonal antibodies may be produced by methods known in the art. These methods include the immunological method described by Kohler and Milstein, Nature 256:495–497 (1975) and by Campbell, in Burdon et al., eds, *Laboratory Techniques in Biochemistry and Molecular Biology*, Vol. 13, Elsevier Science Publishers, Amsterdam (1985); as well as the recombinant DNA method described by Huse et al. (1989).

To produce monoclonal antibodies, a host mammal is inoculated with a peptide or peptide fragment as described above, and then boosted. Spleens are collected from inoculated mammals a few days after the final boost. Cell suspensions from the spleens are fused with a tumor cell in accordance with the general method described by Kohler and Milstein (1975). See also Campbell (1985). To be useful, a peptide fragment must contain sufficient amino acid residues to define the epitope of the molecule being detected.

If the fragment is too short to be immunogenic, it may be conjugated to a carrier molecule. Some suitable carrier molecules include keyhole limpet hemocyanin and bovine serum albumin. Conjugation may be carried out by methods known in the art. One such method is to combine a cysteine residue of the fragment with a cysteine residue on the carrier molecule.

Methods for making chimeric and humanized antibodies are also known in the art. For example, antibodies can be engineered using genetic techniques to produce chimeric antibodies including protein components from two or more species.

For example, methods for making chimeric antibodies include those described in U.S. patents by Boss (Celltech) and by Cabilly (Genentech). See U.S. Pat. Nos. 4,816,397 and 4,816,567, respectively. Methods for making humanized antibodies are described, for example, in Winter, U.S. Pat. No. 5,225,539, Co et al., Nature 351, 501–502 (1992); Queen et al., Proc. Natl. Acad. Sci. 86, 10029–1003 (1989) and Rodrigues et al., Int. J. Cancer, Supplement 7, 45–50 (1992).

Methods are also known for inducing expression of engineered antibodies in various cell types, such as mammalian and microbial cell types. Numerous techniques for preparing engineered antibodies are described, for example, in Owens and Young, "The genetic engineering of monoclonal antibodies," J. Immunol. Meth. 168, 149–165 (1994).

Methods for making single chain antibodies are also known in the art. Some suitable examples include those described by Wels et al. in European patent application 502 812 and Int. J. Cancer 60, 137–144 (1995).

Assays for directly detecting the presence of Y2H14 and its functional equivalents with antibodies follow known formats, such as, fluorescent activated flow cytometry, fluorescent microscopy, and immuno-electron microscopy. Moreover, assays for detecting the presence of proteins with antibodies have been previously described and follow known formats, such as standard blot and ELISA formats. These formats are normally based on incubating an antibody with a sample suspected of containing the protein and detecting the presence of a complex between the antibody and the protein. The antibody is labeled either before, during, or after the incubation step. The protein is preferably immobilized prior to detection. Immobilization may be accomplished by directly binding the protein to a solid surface, such as a microtiter well, or by binding the protein to immobilized antibodies.

Suitable assays are known in the art, such as the standard ELISA protocol described by R. H. Kenneth, "Enzyme-linked antibody assay with cells attached to polyvinyl chloride plates" in Kenneth et al., *Monoclonal Antibodies*, Plenum Press, New York, pp. 376 et seq. (1981).

EXAMPLES

Example 1

Y2H14 Binds IKKα

A yeast two hybrid screen was undertaken with IKKα as a bait in an attempt to identify interacting proteins which could represent in vivo regulators of the cytokine induced kinase cascade. Full length IKKα and smaller fragments in the Field's pGTB9c bait vector (see Fields and Sternglanz, Trends Genet. 10, 286–292 (1994)) met with technical problems owing to its inherent in vivo transactivation properties. These problems were overcome by incorporating a high dose of an inhibitor of the product of the His3 selection gene thereby severely restricting yeast colony growth. (Triazole or 3-AT (3-amino-1, 2, 4-triazole or aminotriazole) has been reported to competitively inhibit the product of the yeast His3 gene in a dose dependent manner (Klopotowski et al., Arch. Biochem. Biophys. 112, 562–566 (1965)). The bait vector's insert was a 937 bp SnaBl/XhoI fragment of the murine IKKα clone encoding the protein's leucine zipper, helix-loop-helix and carboxyl terminus. The latter bait vector was transfected into the Y153 yeast strain and a colony that grew on agar without tryptophan was selected for further transfections according to standard protocols (Yeast Matchmaker manual, Clontech Inc., Palo Alto, Calif.). Yeast harboring the bait grew on histidine-minus plates. However, this non-specific growth was abrogated by the inclusion of 50 μM (3-AT) that would also yield the strongest interactors. Y153 cells harboring the bait vector were transfected with a B lymphoblast cDNA library ($0.6 \times 10^9$ cfu, ATCC #87003) (Durfee et al., Genes Dev 7, 555–569 (1993)) sub-cloned into plasmid BNN132 (for a final transfection frequency of $10^5$ clones), which were spread onto 30 agar plates (His-, Trp-, Leu-, 50 mM 3-AT). 126 clones showing a faster growth rate compared to background colonies were picked after 3 and 6 days incubtion at 30° C. and replated. 70 clones were selected for plasmid isolation based on their growth on His-, Trp-, Leu-, 50 μM 3-AT plates. From these 70 picks secondary picks, 16 clones remained positive after multiple rounds of purification and rescreening (14 of these sixteen were unique and two were isolated twice).

TABLE 1

Results of a Yeast Two-Hybrid Screen with IKKα Helix-Loop-Helix and Leucine Zipper Domains as Bait

| Y2h Clones | Relative Interaction Strength | Insert Length | Identity |
| --- | --- | --- | --- |
| 11 | + | 0.8 kB | RanBP5 |
| 52[#] | ++ | 0.9 kB | CoA Reductase |
| 21 | ++ | 1.3 kB | TRIP9/HuIκBβ2 |
| 29[#] | ++ | 1.1 kB | HuTCP-1 |
| 31 | ++ | 1.5 kB | Hsp40 |
| 37 | + | 2.3 kB | BS4 (Interferon Induced Protein) |
| 67 | + | 1.5 kB | Phospholipase A2 |
| 71 | + | 0.8 kB | Calmodulin |
| 70 | + | 1.5 kB | HuSgn3 |

TABLE 1-continued

Results of a Yeast Two-Hybrid Screen with IKKα Helix-Loop-Helix and Leucine Zipper Domains as Bait

| Y2h Clones | Relative Interaction Strength | Insert Length | Identity |
|---|---|---|---|
| 14* | ++ | 1.2 kB | HuAD3 Locus |
| 35* | +++ | 1.2 kB | Cosmid near Btk |
| 56* | +++ | 0.9 kB | p33ING1-like |
| 53* | +++ | 1.2 kB | Unknown |
| 61** | + | 0.7 kB | Unknown |

Legend: Fourteen yeast two hybrid clones obtained from a human B lymphoblastoid cell cDNA library which specifically interact with the contiguous helix-loop-helix and leucine zipper domains of the IKKα protein. Most clones (Y2h 11,21,29,70,14,35,56 and 53) also bound to an analogous IKKβ bait with similar or even greater strength except for Hsp40 which only specifically bound to the IKKα bait. All clones reproducibly failed to significantly interact with an empty bait vector and two other bait vectors harboring either the IKKα Leucine Zipper or Helix-Loop-Helix domains. The relative interaction strengths are based on the growth rates (i.e., colony size) of each clone. #Isolated Twice; *unknown strong interacting proteins; **Unknown weak interacting protein.

The fourteen clones are shown in Table 1. These results demonstrate the presence of a family of IKKα binding proteins. Nine of the 14 clones are known proteins and the remaining five specify novel proteins: three of which interact with the bait more strongly than IKKα's IκBβ substrate (Y2h35, 53 and 56), one in a comparable fashion to IκBβ (Y2h14) and one exhibited weaker binding (Y2h61). Several of the known proteins are involved in either signaling and/or molecular trafficking pathways in cells. RanBP5 was isolated as a Ran binding protein and Ran is a small GTP-binding and- hydrolyzing protein predominantly located in the nucleus (Deane et al., Mol. Cell Biol. 17, 5087–5096 (1998). RanBP5 is related to importin-β, a mediator of nuclear localization signal (NLS)-dependent nuclear transport. TRIP9/HuIκBβ2 is the predominant isoform of IκBβ in human cells and a known physiological substrate of the IKKα kinase (Lee et al., Mol. Endocrinol. 9, 243–254 (1995); Hirano et al., Mol. Cell. Biol. 18, 2596–2607 (1998)). The presence of IκBβ amongst these IKKα interacting proteins validates the specificity of the screen and also demonstrates the IκBs do not require the IKKα amino terminal kinase domain for binding. Hsp40 and TCP-1 are chaperone proteins which might bind to the bait due to a partially unfolded conformation (in the context of a Gal4dbd chimera). A database of frequently isolated clones in yeast two hybrid screens does contain several hsp proteins but Hsp40 and TCP1 are not represented amongst these frequently isolated, presumably false positive genes. Alternatively, they may also be natural interactors of IKKα that might be involved in its in vivo cytoplasmic trafficking. HuSgn3 was recently described as a component of a 450 kDa protein complex that also possesses an IκB kinase activity. Seeger et al., FASEB J. 12, 469–478 (1998). Sgn3 also exhibited sequence similarities to regulatory components of the 26S proteasome complex. Calmodulin is the principal calcium sensor in the cell, which when complexed to two calcium ions, acts as a regulator for a variety of intracellular enzymes including kinases such as CaM-kinase II, the serine/threonine specific phosphatase, Calcineurin and proteins which maintain the cytoskeletal architecture.

Y2H14 is encoded by a novel transcript expressed within the HuAD3 lolus which has been associated with early onset Alzheimer's disease (Sherrington et al., Nature 375, 754–760 (1995).

What is claimed is:

1. An isolated nucleic acid molecule that encodes an IKK binding protein having SEQ ID NO:1 or a functional equivalent thereof.

2. An isolated nucleic acid molecule according to claim 1 comprising SEQ ID NO:2, or sequences substantially homologous thereto.

3. An isolated nucleic acid molecule according to claim 1 comprising SEQ ID NO:2.

4. An isolated nucleic acid molecule that hybridizes under stringent conditions to a nucleic acid molecule of SEQ ID NO:2.

5. An isolated nucleic acid molecule complementary to the nucleic acid molecule of SEQ ID NO:2.

6. The nucleic acid molecule of claim 2, wherein the substantially homologous nucleic acid sequences are about 40% identical.

* * * * *

UNITED STATES PATENT AND TRADEMARK OFFICE
CERTIFICATE OF CORRECTION

PATENT NO.   : 6,365,722 B1
DATED        : April 2, 2002
INVENTOR(S)  : Marcu, Kenneth It is certified that error appears in the above-identified patent and that said Letters Patent is hereby corrected as shown below:

Title page,
Item [74], now reads "Hoffman & Baron, L.L.P." should read
-- Hoffmann & Baron, L.L.P. --

Column 1,
Line 17, now reads "IκBS" should read -- IκBSs --

Column 3,
Line 67, now reads "thereof Nucleic acid" should read -- thereof. Nucleic acid --

Column 6,
Line 6, now reads "nucleotide(s) other those in which" should read
-- nucleotide(s) other than those in which --

Signed and Sealed this

Twelfth Day of November, 2002

Attest:

Attesting Officer

JAMES E. ROGAN
Director of the United States Patent and Trademark Office